United States Patent [19]

Shubkin et al.

[11] 4,376,222
[45] Mar. 8, 1983

[54] CHEMICAL PROCESS

[75] Inventors: Ronald L. Shubkin, West Bloomfield; Marguerite S. Baylerian, Huntington Woods, both of Mich.

[73] Assignee: Ethyl Corporation, Richmond, Va.

[21] Appl. No.: 218,068

[22] Filed: Dec. 19, 1980

[51] Int. Cl.³ .......................... C07C 2/74; C07C 2/02
[52] U.S. Cl. .................................. 585/255; 585/525
[58] Field of Search ................................. 585/255, 525

[56] References Cited

U.S. PATENT DOCUMENTS 3,763,244 10/1973 Shubkin ................................ 585/18
3,780,128 12/1973 Shubkin ................................ 585/12
4,066,715 1/1978 Isa et al. ............................... 585/532
4,213,001 7/1980 Madgavkar et al. ................ 585/525
4,219,691 8/1980 Mandai et al. ...................... 585/532
4,239,930 12/1980 Allphin et al. ...................... 585/525

Primary Examiner—Curtis R. Davis
Attorney, Agent, or Firm—Donald L. Johnson; Joseph D. Odenweller; Teresa M. Stanek

[57] ABSTRACT

A process for producing hexene-1 oligomer by a process which comprises oligomerizing hexene-1 in the presence of a Friedel-Crafts catalyst, such as boron trifluoride, and a promoter, such as water, the improvement comprising dissolving hexene-1 in a hydrocarbon solvent comprising 10–75% of the reaction mixture and conducting the oligomerizing in the hydrocarbon solvent. The hydrocarbon solvent has a minimum boiling point of 60° C. There is an increase in both the reaction rate and trimer yield of product.

5 Claims, No Drawings

CHEMICAL PROCESS

BACKGROUND OF THE INVENTION

This invention relates to the preparation of hexene-1 oligomer by the oligomerization of hexene-1 in the presence of a Friedel-Crafts catalyst and promoter. More particularly, the invention is concerned with the addition of a hydrocarbon solvent, such as n-nonane or saturated hexene-1 oligomer product to hexene-1 in the presence of a boron trifluoride ($BF_3$) and water catalyst system. Hexene-1 oligomer may be used in very light lubricating oils, more specifically hexene-1 oligomer may be used as an emollient in cosmetic preparations.

A variety of Friedel-Crafts catalysts have been used in the oligomerization of 1-olefins. The use of an aluminum halide and promoter is well known. U.S. Pat. No. 4,066,715 and U.S. Pat. No. 4,219,691 suggest the use of an optional solvent to dilute the reaction mixture as well as achieve easy control of the reaction temperature.

$BF_3$-catalyzed oligomerizations of $C_{6-16}$ n-α-olefins are well known. U.S. Pat. No. 3,763,244 employs a water co-catalyst and U.S. Pat. No. 3,780,128 suggests using an alcohol co-catalyst. The use of a solvent is not recommended since this would require the addition of a separation procedure to remove the solvent from the system.

A variety of co-catalysts or promoters have been recognized which are beneficial in $BF_3$ catalyzed systems. For example, U.S. Pat. No. 4,213,001 describes a process for oligomerizing a 1-olefin having 6-12 carbon atoms or a mixture thereof in a suspension of a powdered solid adsorbent. A two-fold advantage is obtained. The catalyst disposal problem is eliminated and a high trimer yield of product results. In addition to this co-catalyst, the use of an inert solvent is said to be possible. The solvent is said to slow down the various reaction rates. Likewise, U.S. Pat. No. 4,066,715 discloses that a solvent may be used to control the reaction temperature. Also, U.S. Pat. No. 4,219,691 uses a solvent to reduce viscosity and control temperature. There is no disclosure of the use of a solvent with hexene-1.

Surprisingly, it has now been discovered that the addition of a hydrocarbon solvent to a hexene-1 oligomerization reaction in the presence of a Friedel-Crafts catalyst and suitable promoter results in an increased reaction rate and improved yield of trimer product. More particularly, a $BF_3$ catalyzed oligomerization of hexene-1 proceeds with $BF_3$ (gas) and $BF_3 \cdot 2H_2O$ complex in a hydrocarbon solvent at atmospheric pressure to achieve an increased reaction rate and improved trimer yield. A more expensive promoter such as a solid adsorbant or an alcohol is not necessary.

SUMMARY

In accordance with the present invention the process of oligomerizing hexene-1 in the presence of a Friedel-Crafts catalyst such as $BF_3$ and suitable promoter such as water can be improved by the addition of a hydrocarbon solvent. Advantages include an increased reaction rate and an increased yield of trimer product.

DESCRIPTION OF THE PREFERRED EMBODIMENTS

A preferred embodiment of the present invention is an improvement in a process for producing hexene-1 oligomer by a process which comprises oligomerizing hexene-1 in the presence of a Friedel-Crafts catalyst and promoter, distilling off the monomer and dimer and hydrogenating the residual product, the improvement comprising dissolving hexene-1 in a hydrocarbon solvent comprising 10-75% of the reaction mixture and conducting said oligomerizing in said solvent, said hydrocarbon solvent having a boiling point of at least about 60° C. whereby the oligomerization rate is substantially increased. More preferably, the hydrocarbon solvent constitutes 20-50% of the reaction mixture.

The initial hexene-1 may be pure or contain minor impurities. Exemplary of these impurities are hexene-2, hexene-3, pentene-2, heptene-1, octene-1, octene-3, and decene-2. Preferably, these minor impurities will comprise less than 20% of the initial hexene-1 mixture. More preferably, these minor impurities will be limited to less than 10% of the hexene-1 mixture.

The Friedel-Crafts catalyst employed in this invention can be selected from the group consisting of $AlCl_3$, $BF_3$, $TiCl_4$, and $FeBr_3$. Preferably, the catalyst is $BF_3$.

The amount of $BF_3$ used in this process should be a catalytic amount. This is an amount which when used in the presence of a co-catalyst will cause the reaction to proceed at a reasonable rate. A useful range of $BF_3$ is from about 0.15-15 parts per 100 parts of hexene-1 monomer.

A promoter or co-catalyst is necessary when dealing with Friedel-Crafts catalyzed oligomerizations of α-olefins in order to obtain useful catalytic activity. Included in the list of substances which have been recommended for co-catalysts are water, silica gel, aliphatic ethers such as dimethyl ether and diethyl ether, aliphatic alcohols such as methanol, ethanol, n-butanol and propanol, polyols such as ethylene glycol and glycerol, aliphatic carboxylic esters, ketones, aldehydes and acid anhydrides. Preferably, the promoter is water. The amount of promoter ranges from 0.05 to 0.5 mole percent of initial hexene-1. Preferably, the promoter is 0.1 to 0.2 mole percent hexene-1.

The actual catalyst specie is believed to form from the interaction between the Friedel-Crafts catalyst and co-catalyst. For example, whenever reference is made to the use of a water-promoted boron trifluoride or that the reaction is carried out in its presence, it is meant that the actual catalyst specie that is used is the specie that forms in the oligomerization system when boron trifluoride and the water co-catalyst are added to the system.

The $BF_3$ catalyzed oligomerization of hexene-1 yields a mixture of hexene-1 monomer, dimer, trimer, tetramer and higher oligomers. The monomer and dimer are usually distilled off and the remaining higher oligomers are hydrogenated in the presence of a suitable hydrogenation catalyst under appropriate reaction conditions. Nickel on kieselguhr is a frequently employed hydrogenation catalyst.

Preferably, the hydrocarbon solvent used in this invention is composed of $C_{6-12}$ branched or linear aliphatic hydrocarbons or a mixture thereof having a boiling point of at least about 60° C. Exemplary of such hydrocarbons are hexane, ligroin, octane, isooctane, nonane, decane and dodecane. More preferably, the hydrocarbon solvent selected is n-nonane.

The use of n-nonane as the hydrocarbon solvent offers several advantages. Hexane has a lower molecular weight and produces a smaller increase in reaction rate of oligomerization of hexene-1 in the presence of $BF_3$ and water. A larger amount of undesirable dimer is also formed with hexane compared to nonane.

Higher molecular weight aliphatic hydrocarbon solvents may successfully improve trimer yield and provide for an increased reaction rate, however, increased cost and difficulties of product separation make them less desirable.

Still more preferred is the use of a hydrocarbon solvent of saturated hexene-1 oligomer comprising saturated hexene-1 trimer, tetramer and higher oligomers. After the oligomerization of hexene-1 monomers, the monomer and dimer reaction products are removed by distillation. The remaining higher oligomers are hydrogenated in the presence of an appropriate hydrogenation catalyst. It is this saturated higher oligomer product which is useful as a hydrocarbon solvent for the initial hexene-1 oligomerization step. For this purpose the saturated hexene oligomer must be added at the start of the reaction.

The obvious advantage of using the hexene-1 oligomer product as a solvent for the initial oligomerization step is the elimination of a separation procedure. In this case, the hydrocarbon solvent itself is the desired reaction product.

Without limiting the invention in any manner and without advocating any particular mechanism or theory of action, it is believed that the advantages obtained by the use of the hydrocarbon solvent are due to increased solubility of the promoted $BF_3$ catalyst in the solvent-containing reaction mass.

The process of this invention is carried out using the usual conditions of $BF_3$ catalyzed polymerization of $\alpha$-olefins. The reaction is conducted at a temperature low enough to cause the reaction to proceed at a reasonable rate yet not so high as to adversely affect the course of the reaction. The temperature is generally between 20° C.-60° C. and preferably it is between 20° C.-50° C. The preferred reaction conditions include a pressure of from about 1.0 psig to 10 psig, and preferably the pressure is between 1.0 psig and 1.5 psig.

EXAMPLE

In a reaction vessel was placed 100.0 g hexene-1 and 100.0 g n-nonane. The system was stirred and sparged with $BF_3$ (gas) for approximately five minutes until the liquid was saturated. While continuing to bubble $BF_3$ (gas) through the system, 0.075 ml $BF_3 \cdot 2H_2O$ complex was added.

The reaction progress was monitored by periodic withdrawal of small aliquots of the reaction mixture which were analyzed by both viscosity measurements and vapor phase chromatography.

When the reaction was deemed to be complete, the mixture was quenched with 100 ml water, washed two times with 100 ml dilute ammonium hydroxide and then washed with 100 ml portions of water until the washes were neutral. Excluding solvent vapor phase chromatography indicated 0.35% monomer, no dimer, 49.21% trimer, 40.37% tetramer and 8.79% pentamer.

The monomer, dimer and n-nonane can be distilled off and this product hydrogenated to obtain a saturated hexene oligomer which is especially useful as an emollient in cosmetic formulations.

The table below depicts a variety of solvents which were used in this invention. The catalyst system employed in each case is $BF_3$ (gas) and $BF_3 \cdot 2H_2O$ (complex) and the process was substantially the same as Example 1.

| Solvent | Solvent (wt %) | Water Co-catalyst (mole % of hexene-1) | Time (minutes) | PRODUCT COMPOSITION (VPC AREA %) | | | |
|---|---|---|---|---|---|---|---|
| | | | | Monomer | Dimer | Trimer | Higher Oligomers |
| none | — | 0.2 | 225 | 0.98 | 13.52 | 61.03 | 23.88 |
| n-hexane | 50 | 0.2 | 195 | 0.51 | 13.26 | 67.74 | 18.49 |
| n-decane | 50 | 0.2 | 135 | 0.59 | 2.25 | 69.80 | 27.35 |
| n-nonane | 50 | 0.2 | 105 | 0.34 | 1.78 | 68.40 | 29.48 |
| n-nonane | 25 | 0.2 | 80 | — | 0.21 | 76.58 | 22.59 |
| n-nonane | 25 | 0.1 | 180 | 0.48 | 10.55 | 67.40 | 21.21 |
| ligroin | 25 | 0.2 | 170 | 0.42 | 11.02 | 65.90 | 19.75 |
| recycled hydrogenated product | 25 | 0.2 | 160 | 0.29 | 7.98 | 69.24 | 21.72 |
| recycled hydrogenated product | 50 | 0.2 | 70 | — | 3.23 | 62.98 | 30.83 |

We claim:

1. In a process for producing saturated hexene-1 oligomer by a process which comprises oligomerizing hexene-1 in the presence of a Friedel-Crafts catalyst and promoter, distilling off the monomer and dimer and hydrogenating the residual product, the improvement comprising dissolving hexene-1 in said hydrogenated residual product comprising 10-75% of the reaction mixture and conducting said oligomerizing in said hydrogenated residual product whereby the oligomerization rate is substantially increased.

2. A process as recited in claim 1 wherein said promoter is water.

3. A process as recited in claim 1 wherein said hydrogenated residual product constitutes 20-50% of the initial reaction mixture.

4. In a process for producing saturated hexene-1 oligomer by a process which comprises oligomerizing hexene-1 in the presence of boron trifluoride and water, distilling off the monomer and dimer and hydrogenating the residual product, the improvement comprising dissolving hexene-1 in said hydrogenated residual product comprising 10-75% of the reaction mixture and conducting said oligomerizing in said hydrogenated residual product whereby the oligomerization rate is substantially increased.

5. A process as recited in claim 4 wherein said hydrogenated residual product constitutes 20-50% of the initial reaction mixture.

* * * * *